(12) United States Patent
Hutchinson et al.

(10) Patent No.: US 7,991,627 B2
(45) Date of Patent: Aug. 2, 2011

(54) INJECTED DRUG IDENTIFICATION AND FAIL-SAFE SYSTEM

(75) Inventors: George Martin Hutchinson, Milwaukee, WI (US); Neal Joseph Sandy, Middleton, WI (US); Russel Craig Ward, Sun Prairie, WI (US); Ronald Peter Makin, Fitchburg, WI (US); William Scott Sutherland, Haverhill, MA (US)

(73) Assignee: General Electric Company, Schenectady, NY (US)

( * ) Notice: Subject to any disclaimer, the term of this patent is extended or adjusted under 35 U.S.C. 154(b) by 1100 days.

(21) Appl. No.: 11/443,825

(22) Filed: May 31, 2006

(65) Prior Publication Data

US 2006/0287887 A1     Dec. 21, 2006

Related U.S. Application Data

(63) Continuation-in-part of application No. 11/157,415, filed on Jun. 21, 2005, now abandoned.

(51) Int. Cl.
   G06Q 50/00     (2006.01)
   G06Q 10/00     (2006.01)

(52) U.S. Cl. .............................................. 705/3; 705/2

(58) Field of Classification Search .................... 705/2–3
   See application file for complete search history.

(56) References Cited

U.S. PATENT DOCUMENTS

| | | | |
|---|---|---|---|
| 5,153,827 A | 10/1992 | Coutre et al. | |
| 6,519,569 B1 | 2/2003 | White et al. | |
| RE38,189 E | 7/2003 | Walker et al. | |
| 6,807,965 B1 * | 10/2004 | Hickle | 128/204.23 |
| 6,868,344 B1 * | 3/2005 | Nelson | 702/31 |
| 7,256,888 B2 * | 8/2007 | Staehr et al. | 356/319 |
| 2001/0040127 A1 | 11/2001 | Donig et al. | |
| 2001/0056358 A1 * | 12/2001 | Dulong et al. | 705/2 |
| 2003/0074223 A1 * | 4/2003 | Hickle et al. | 705/2 |
| 2003/0204330 A1 | 10/2003 | Allgeyer | |
| 2004/0176984 A1 | 9/2004 | White et al. | |

FOREIGN PATENT DOCUMENTS

WO    2005/046766 A1    5/2005
WO    2005/118054 A1    12/2005

OTHER PUBLICATIONS

Search Report dated Sep. 14, 2007.
Office Action mailed Mar. 31, 2009.
Office Action mailed Sep. 28, 2009.

* cited by examiner

*Primary Examiner* — Luke Gilligan
*Assistant Examiner* — Joy Chng
(74) *Attorney, Agent, or Firm* — Andrus, Sceales, Starke & Sawall, LLP

(57) ABSTRACT

The present invention is a system and method of pre-delivery drug identification. The system and method is implemented where drugs are being administered, such as in a hospital or clinic, and identifies the drug being administered to the patient before the drug reaches the patient. The system and method may utilize a sensor used for other physiologic monitoring to identify the drug. After identification, the system and method is configured to cross-reference the identified drug with the patient's prescription and allergy information, and to prevent delivery to the patient, if necessary. The system and method also utilizes data collected from the patient with a physiological monitor or a ventilator sensor to further determine whether the drug is appropriate for the patient. The method and system may also include an override system for medical personnel. The method described may be carried out by a software application.

17 Claims, 4 Drawing Sheets

INJECTED DRUG IDENTIFICATION AND FAIL-SAFE SYSTEM

RELATED APPLICATIONS

This is a continuation-in-part application claiming priority under 35 U.S.C.§120 of the co-ending U.S. patent application Ser. No. 11/157,415 filed on Jun. 21, 2005 now abandoned entitled "PRE-DELIVERY DRUG IDENTIFICATION SYSTEM." The U.S. patent application Ser. No. 11/157,415 filed on Jun. 21, 2005 and entitled "PRE-DELIVERY DRUG IDENTIFICATION SYSTEM" is also hereby incorporated by reference.

FIELD OF THE INVENTION

The invention relates to the filed of drug delivery. More particularly, the invention relates to the filed of identifying and confirming drug dosages before administering them to a patient.

BACKGROUND OF THE INVENTION

Inappropriate administration of injected medications via syringe and IV tubing is a well documented and serious problem. Administering a completely wrong drug can arise from syringe swapping or mislabeling. Inappropriate drug administration can also arise from a clinician giving a drug to address one problem or to invoke a response while being unaware of a potentially serious contraindication. For instance, administering a bolus of morphine to relieve pain in a patient whose cardiovascular condition is already compromised can be fatal.

A November 1999 Institute of Medicine report states that "The medication process provides an example where implementing better systems will yield better human performance. Medication errors now occur frequently in hospitals, yet many hospitals are not making use of known systems, nor are they actively pursing new safety systems."

There has been significant effort in developing systems that are process focused such as bar coding and radiofrequency "tagging" of drugs. Since these methods are process focused, they are inherently prone to error, even though they are an improvement to systems without such processes. Only the identification of the drug itself will insure that the proper drug is being delivered to the patient.

SUMMARY OF THE INVENTION

The present invention is a system and method of pre-delivery drug identification. The system and method is implemented where drugs are being administered, such as in a hospital or clinic, and identifies the drug being administered to the patient before the drug reaches the patient. The system and method may utilize a sensor used for other physiologic monitoring to identify the drug. After identification, the system and method is configured to cross-reference the identified drug with the patient's prescription and allergy information, and to prevent delivery to the patient, if necessary. The system and method also utilizes data collected from the patient with a physiological monitor or a ventilator sensor to further determine whether the drug is appropriate for the patient. The method and system may also include an override system for medical personnel. The method described may be carried out by a software application.

A method of pre-delivery drug identification, the method comprises receiving a drug sample from a drug source into a drug identification unit, identifying the drug sample with the drug identification unit, collecting a set of patient physiological data with a monitoring device, cross-referencing the identified drug sample with the set of physiological data such that the set of physiological data confirms the identified drug sample when the identified drug sample is safe for the patient, and preventing the identified drug sample from being administered to a patient with a delivery prevention unit when the set of physiological data does not confirm the identified drug sample is safe for the patient. The method further comprises cross-referencing the identified drug sample with a set of databases, such that the set of databases are configured to confirm the identified drug sample wherein the drug sample corresponds to a prescription for the patient, confirming identifying step with an RFID tag and an RFID reader, identifying the components, the concentration and the dosage of the drug sample, activating an alarm when the identified drug is prevented from being administered wherein the alarm is any of the following an audible alarm, a visual alarm, and a remote alarm which further comprises overriding the preventing step when the alarm is activated and the identified drug is prevented from being administered to the patient. The drug identification unit is an IR detection system, and wherein the monitoring device is any of the following a physiological monitor, and a ventilator sensor.

The present invention further comprises of a system for pre-delivery drug identification, the system comprising a drug identification unit configured to receive a drug sample from a drug source, wherein the drug identification unit identifies the drug sample, a monitoring device configured to collect a set of patient physiological data from a patient, the monitoring device further configured to allow the drug identification unit to cross-reference the identified drug sample with the set of physiological data, and a delivery prevention unit coupled to the drug identification unit, the delivery prevention unit configured to prevent the drug sample from being administered to the patient when the set of physiological data does not confirm the drug sample is safe for the patient. The system of the present invention further comprises a set of databases coupled to the drug identification unit, configured to allow the drug identification unit to cross-reference the identified drug sample with the set of databases, and wherein the delivery prevention unit is configured to prevent the drug sample from being administered to the patient when the set of database does not confirm the drug sample, the drug sample corresponds to a prescription for the patient, the drug identification unit is configured to identify the components, the concentration and the dosage of the drug sample. The system further comprises an alarm that is activated when the identified drug is prevented from being administered wherein the alarm is any of the following an audible alarm, a visual alarm, and a remote alarm. A physician may override the delivery prevention unit when the alarm is activated and the identified drug is prevented from being administered to the patient. The system also comprises an RFID tag and an RFID reader configured to confirm the identification of the drug sample and wherein the drug identification unit is an IR detection system. The system's monitoring device may be a physiological monitor and a ventilator sensor.

DETAILED DESCRIPTION

Figure 1B:
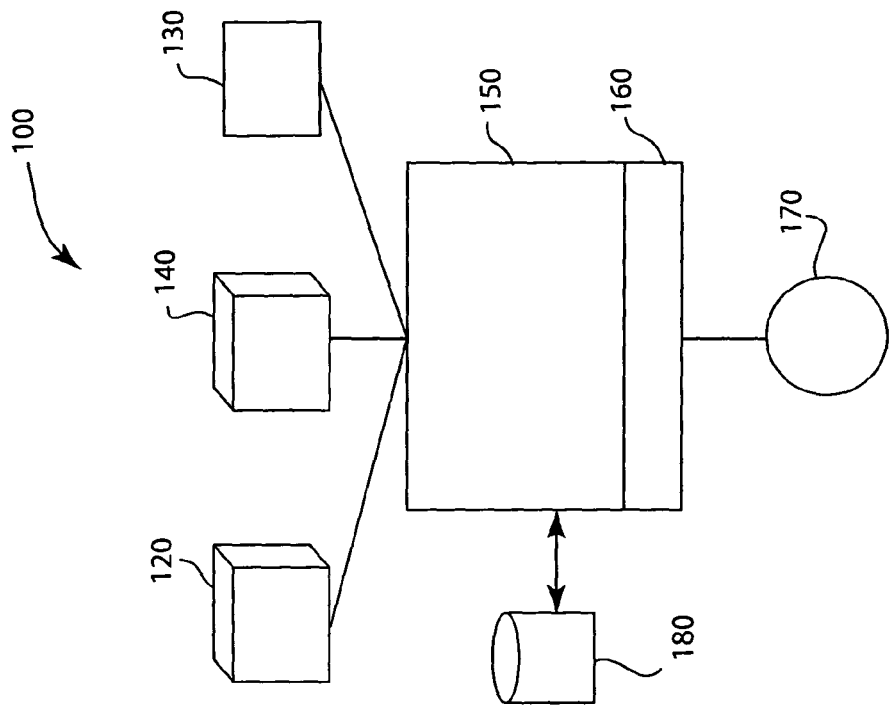
FIG. 1A-FIG. 1D are block diagrams illustrating embodiments of the system of the present invention.

The drug identification system and method identifies the drug prior to delivery to a patient. The identification system identifies the compound and/or concentration, cross-references the identification with the prescription, allergies and interactions databases via an interfaced data management system, and has a means to prevent delivery to the patient. Once the appropriate drug is confirmed, the drug compound can be delivered to the patient. The system will record the compound, when it was given and by which clinician. The system would deploy a stopcock or other line clamping mechanism in order to stop drug flow to the patient prior to actual delivery. The system may or may not have a means to enunciate or otherwise transmit information about the relative correctness of the drug delivery. The system would alert or alarm in a manner that informs the clinician of a potential adverse drug event. The systems will maintain a record of measured drugs and will allow for single or multiple lines to be analyzed.

The primary advantage of the invention is that it will minimize the number of adverse drug events that occur in hospitals, clinics and surgery centers. This advantage may also be translated to home use, emergency and ambulatory use and use in the military. Because the system is able to identify the concentration and/or the compound of the drug itself, it is the most accurate method of drug identification possible. Systems available today rely on processes that have varying levels of compliance and varying levels of propensity for error. And, since the system is dynamic and linked to a drug library via an information system (for example), it can not only detect the drug, but also determine if the drug should be delivered to the patient by comparing the drug to the prescription order as well as to the patient's condition, allergies, or other physiological information, as they are found on the patient's electronic medical record. The ability to automatically stop the delivery of the drug sets the invention apart from other identification systems as well.

Furthermore, the system's ability to determine drug concentrations is highly advantageous and unique. Because the identification system is in-line, yet non-invasive, the system does not waste any drug, and it measures the specific drug sample that is intended for the patient. An alternative embodiment of the present invention implements a split-stream configuration, wherein the sample from the drug source is routed away from the line, is tested, and does not re-enter the line. Finally, drug mixtures (cocktails) would be easily identified and could be disallowed by the system.

It should also be noted that all current drug identification methods are indirect, meaning the drug itself is not identified. This invention actually identifies the drug. Because the identification system can detect specific drug characteristics, it will also recognize mixtures, thereby allowing for the prevention of drug cocktails. All current drug identification methods do not have a means to determine drug concentrations. This invention has such a capability. All current methods cannot stop the inappropriate delivery of a drug. This invention has the ability to automatically stop the delivery of a drug, thereby preventing adverse drug events. The invention can apply to mechanical drug delivery equipment such as IV delivery devices (volumetric or syringe pump) as well as bolus delivery methods. The detection method is non-invasive to the compound that maintains the purity of the drug.

The system and method uses physiologic data from a patient monitor or sensors in a ventilator or anesthesia delivery system to provide an input that would also control the flow restrictor device. Given that a drug will have physiologic side effects, certain levels of vital signs may point to a contraindication of administering a drug. A drug with a known effect of depressing blood pressure being administered to a patient with a very low blood pressure should result in a flow restriction and a warning. The system and method also includes an alert system that will indicate when the medication is not delivered, along with the rationale for that decision not to deliver. An override means is also incorporated to permit a clinician to deliver the drug based on his or her expert opinion. Also, the drug identification unit can be implemented as a sensor that is used for other physiologic monitoring purposes. For example, an infrared sensor used for blood analyte analysis could be used serially for detecting the identity of the drug.

A drug identification system 100 of the present invention is depicted in FIGS. 1A-1D. In FIGS. 1A-1D, the drug identification system 100 includes a drug identification unit 150 configured to receive a sample of a drug to be administered to the patient 170 from a drug source 110, 120, 130, 140. Multiple embodiments of the present invention include various drug sources such as a volumetric pump 110, a syringe pump 120, 140, or a manual infusion device 130, such as, but not limited to a bolus syringe. It should be noted that the drug source 110, 120, 130, 140 utilized in any embodiment of the present invention is likely to be determined by the preference of the physician, the standard practice of the region and/or the particular drug or type of care being administered. Furthermore, referring to FIG. 1B, particular embodiments may utilize more than one particular type of drug source such as a first syringe pump 120 and a second syringe pump 140. As is well known in the art, volumetric pumps 110 and syringe pumps 120, 140 are metered drug delivery sources, while a manual infusion device 130 is not of the metered variety.

Still referring to FIGS. 1A-1D, when a physician prescribes a drug to be administered to a patient 170, one of the aforementioned drug sources 110, 120, 130, 140 is utilized to deliver the drug to the patient 170. The drug identification system 100 of the present invention contemplates receiving a drug sample from the drug source 110, 120, 130, 140 into a drug identification unit 150. The drug identification unit 150 is able to test the drug sample from the drug source 110, 120, 130, 140 and determine a number of characteristics of the drug sample. The drug identification unit 150 is able to identify the element or compound of the drug sample, the concentration of the drug sample, as well as the dosage of the drug sample.

In one embodiment of the present invention, the drug identification unit 150 utilizes raman scattering spectroscopy as a technique to analyze and identify the drug to be administered to the patient 170. The details of raman scattering spectroscopy are included in U.S. Pat. No. 6,868,344 to Nelson. It is further contemplated that other embodiments of the present invention can and will include a drug identification unit 150 utilizing other methods known in the art, or future drug identification methods.

The drug identification unit 150 is coupled to a set of patient databases 180. The drug identification unit 150 cross-references the set of patient databases 180 in order to confirm that the drug sample delivered by the drug source 110, 120, 130, 140 is appropriate and safe for the patient 170. The set of databases 180 includes a prescription database, an allergy database and an interaction database, such that the identified drug sample can be cross-referenced against each of these databases 180. Of course, additional databases can be added or subtracted to the set of patient databases 180 as needed or required. Furthermore, the databases may be configured centrally in a network configuration, or locally to the drug identification system 100. In fact, any database 180 configuration known in the art may be used according to the constraints of the particular drug identification system 100.

The drug identification unit 150 will cross-reference the identified drug sample to determine whether the drug sample matches the prescription written by the physician, and will further cross-reference whether the patient 170 is allergic to the drug sample, and further whether the drug sample would interact with any of the patient's 170 other medications. As stated previously, the drug identification unit 150 is configured to identify not only what the drug sample is made up of, but also the concentration and the dosage of the drug sample, thus allowing the drug identification unit 150 to exactly match the drug sample to the prescription.

Figure 1A:
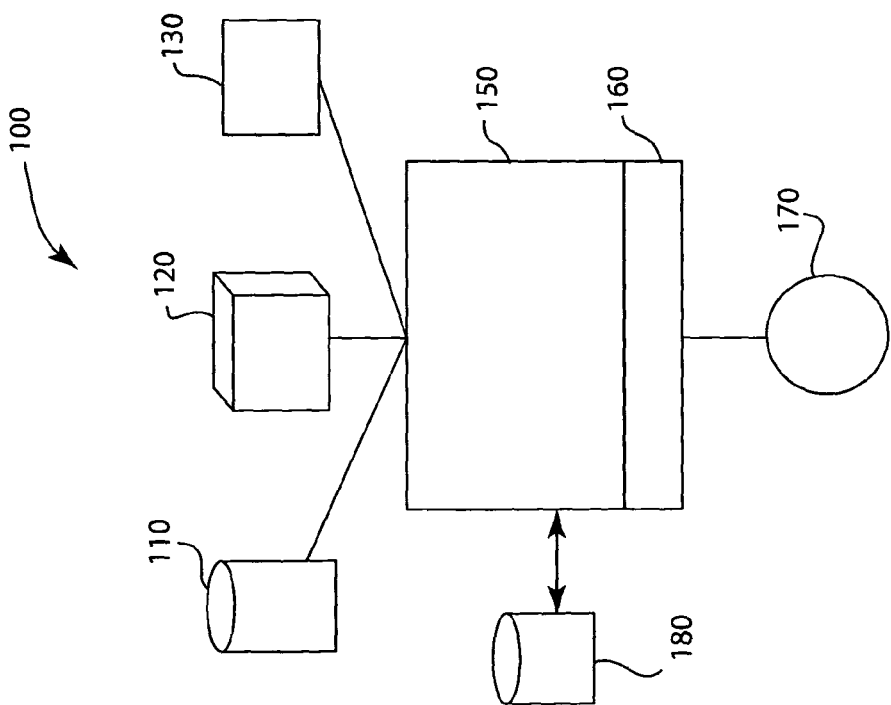
Figure 1D:
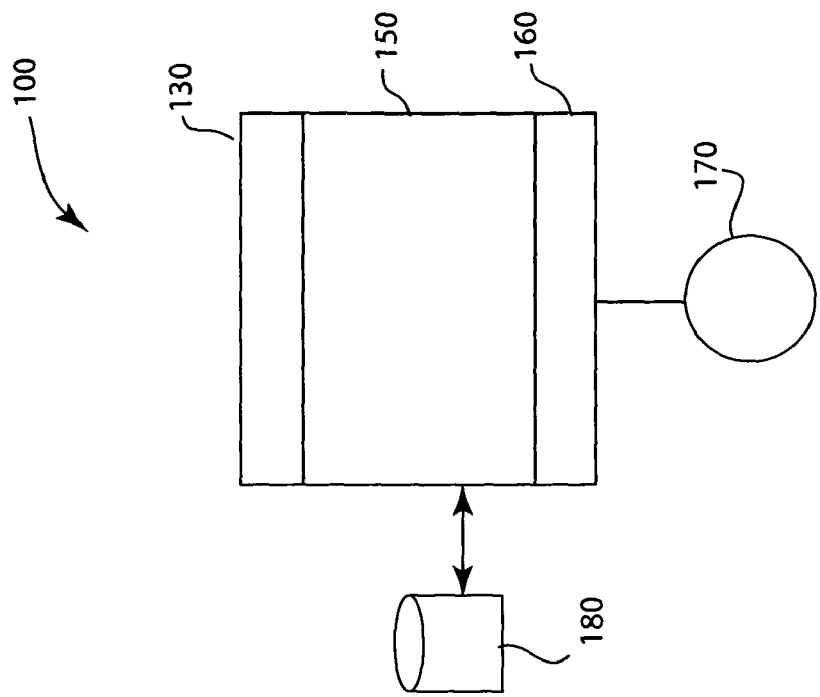
Figure 1C:
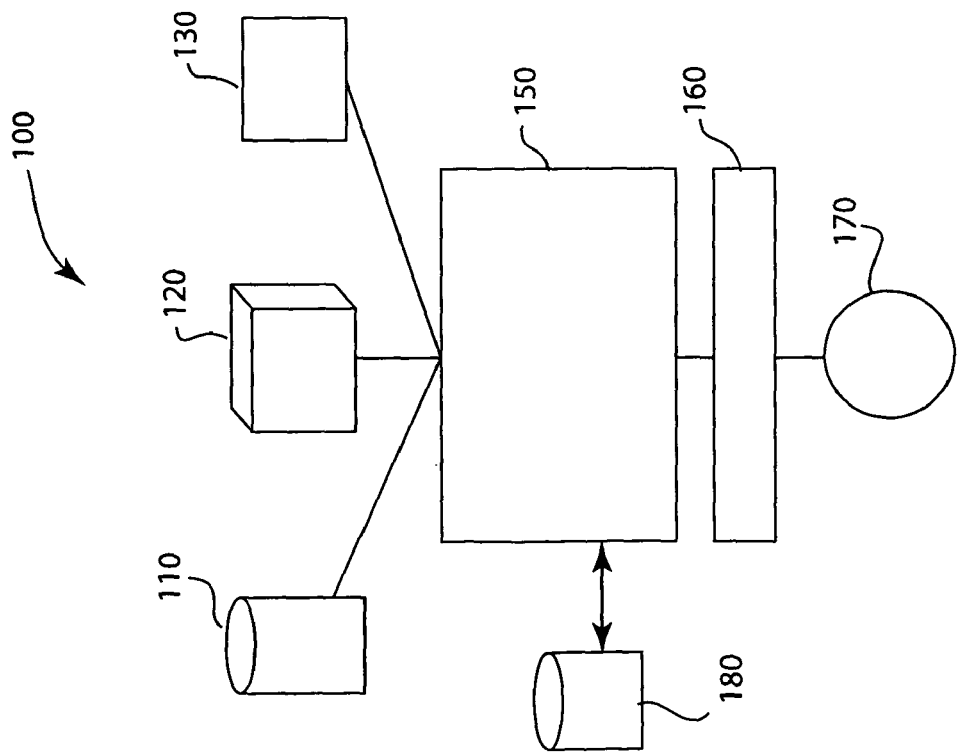

Still referring to FIGS. 1A-1D, the drug identification system 100 of the present invention also includes a delivery prevention unit 160. If the drug identification unit 150, when cross-referencing the identified drug sample to the set of patient databases 180, cannot confirm that the identified drug sample is appropriate and/or safe to administer to the patient 170, the delivery prevention unit 160 will prevent the drug sources 110, 120, 130, 140 from administering the drug to the patient 170. Preferably, the delivery prevention unit 160 is an electronically controlled flow valve, but can also be any IV flow restrictor known or later developed in the art. Only when the drug identification unit 150 is able to cross-reference the set of patient databases 180, and confirm that the drug sample exactly matches the prescription, and is not harmful to the patient, will the drug identification unit prompt the delivery prevention unit 160 to allow the drug to be administered to the patient 170. As is shown in FIGS. 1A, 1B and 1D, preferably the delivery prevention unit 160 is directly coupled to the drug identification unit and is likely implemented with the drug identification unit. Other embodiments, such as that depicted FIG. 1C, will include a delivery prevention unit 160 separate yet coupled to the drug identification unit 150. Referring to FIG. 1D, the drug identification system 100 of the present invention may also be implemented in one unit, including a manual infusion device 130, a drug identification unit 150 and a delivery prevention unit 160. The drug identification 150 will also cross reference the identified drug sample to a set of collected physiological data from the patient as described above.

Figure 2:
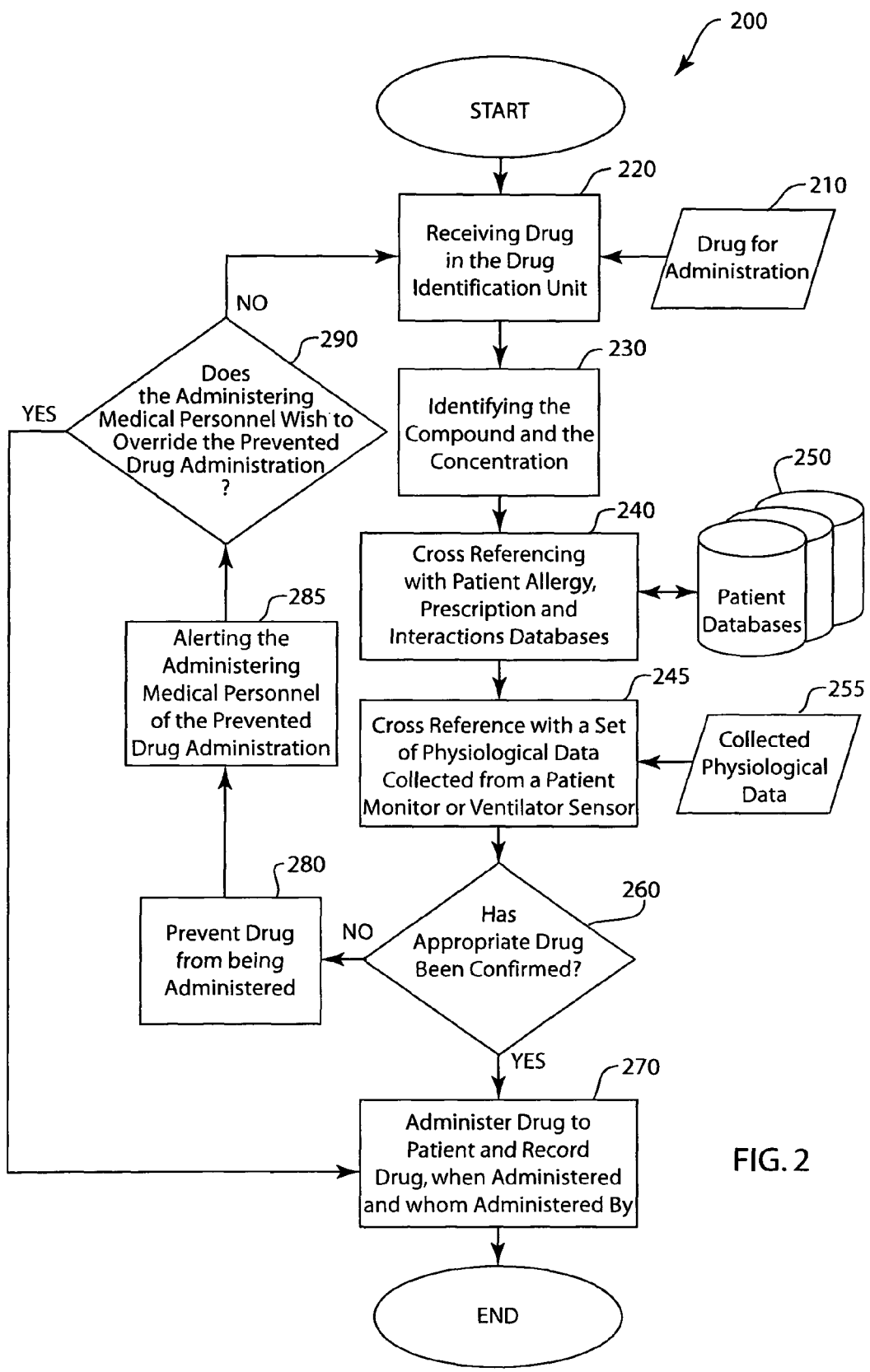
FIG. 2 is a flow chart illustrating an embodiment of the method of the present invention.

Referring now to FIG. 2, a drug identification method 200 of the present invention is depicted. In step 220, the drug for administration 210 to the patient is received in the drug identification unit. In step 230, the drug is identified, including the actual compound, the concentration and the dosage of the drug for administration 210. In step 240, the identified drug is cross-referenced with a set of patient databases 250 to confirm whether the identified drug matches the prescription written by the physician. In step 240, the identified drug is also cross-referenced to the patient databases 150 to determine whether the identified drug will cause problems with the patients due to allergies and/or interactions with other drugs.

In step 245, the identified drug is cross-referenced with a set of collected physiological data 255 that is collected from a patient monitor or a ventilator sensor as described above. This cross-referencing in step 245 determines whether the identified drug will have physiologic side effects, and certain levels of particular vital signs may require that the identified drug not be administered to the patient. In step 260, if the identified drug is not confirmed as the proper prescription or being dangerous to the patient, then in step 280 the identified drug is prevented from being administered to the patient. In step 285, when the drug is prevented from being administered in step 280, the medical personnel administering this drug is alerted of the prevention. The alerting in step 285 may be implemented by an alarm or light within the drug identification system 100, or by remotely alerting the medical personnel via a pager, or personal electronic device, or through other methods known in the art. In step 290, if the medical personnel administering the drug wishes to override the drug administration prevention, then the method 200 proceeds to step 270, where the drug is administered to the patient, and the specifics of the administration including when administered and whom administered by is recorded. If the medical personnel administering the drug do not wish to override the administration prevention in step 290, then the method 200 starts again at step 220.

Following, if the identified drug is confirmed to be appropriate for administration to the patient in step 260, then the drug is administered to the patient in step 270. Furthermore, in step 270, the administration of the identified drug is recorded, and the time and the person who administered the drug is recorded as well.

Figure 3:
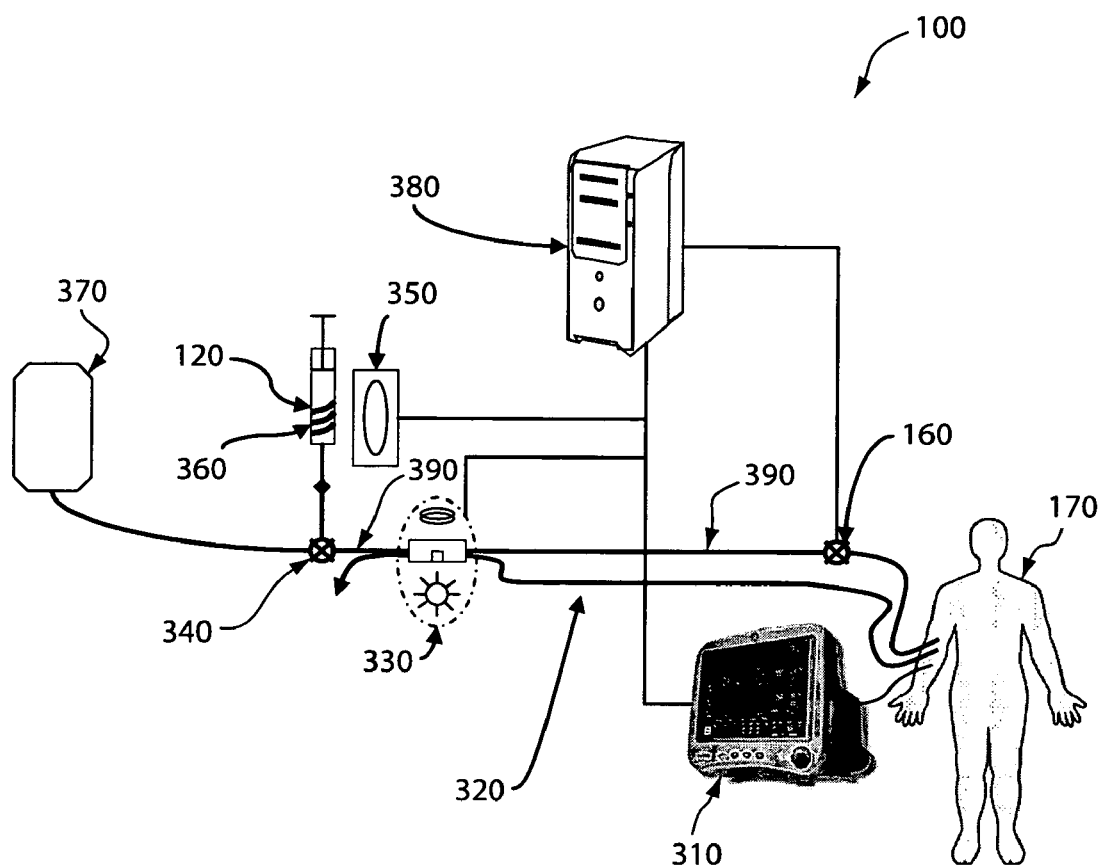
FIG. 3 is a block diagram illustrating an embodiment of the present invention.

FIG. 3 illustrates an embodiment of the drug identification system 100. In this drug identification system 100, the patient 170 is monitored by a physiological monitor 310, which may include any physiological monitor or ventilator sensor that would assist a physician in determining whether a medication being given to the patient 170 is resulting in adverse effect to the patient 170. The drug identification system 100, as depicted in FIG. 3, may also include an existing blood access system 320 having an IR detection system 330 that may act as a stand alone or as an additional drug identification unit 150 (FIGS. 1a-1d). Such an IR detection system 330 is included in blood access systems 320 to examine the patient's 170 blood for content. Such an IR detection system 330 may be utilized to examine the contents of the IV line 390 of the drug identification system 100 only, or be utilized to examine the contents of the IV line 390 as well as the blood access system 320.

Still referring to FIG. 3, an IV solution 370 is administered to the patient 170 with the IV line 390. A first syringe pump 120 having an RFID tag 360 is coupled to the IV line 390 by a flow restrictor device 340 that is controlled manually by medical personnel. The RFID tag 360 includes an identification bar code that may be read by an RFID reader 350. The information regarding the prescribed medication found in the first syringe pump 120 is communicated by the RFID reader 350, the IR detection system 330, the physiological monitoring 310, and any other drug identification unit 150 (not shown) to the computer 380. The computer 380 includes a storage media and a processor, wherein the computer 380 is configured to collect this information and execute a computer program employing the described method above. Furthermore, the computer 380 will control the delivery prevention unit 160, thereby restricting or allowing the prescribed medication to flow to the patient 170.

The drug identification system 100 may also include additional features not shown in FIG. 3. A physician notification means may be implemented to alert the physician or other medical personnel when a prescribed drug has been restricted by the drug identification system 100. Such an alarm may include an audible or visual alarm on the physiological monitor 310 or on another component of the drug identification system 100. The notification means may also include the ability to automatically page the physician or alert the physician through a handheld electronic device. The drug identification system 100 may also include an override mechanism (not shown), which would allow a physician to manually open the delivery prevention unit 160 when the drug identification system 100 prevents the prescribed medication from reaching the patient 170.

This system and method is advantageous as it automatically prevents the inappropriate administration of medication based on both mislabeling and contraindications, thereby greatly reducing the number of use errors in hospitals. In combination with the automatic label reading system (RFID tag 360 and RFID reader 350), this system and method provides a multi-tiered check system prior to the prescribed medication reading the blood stream. The system and method is also advantageous in that after installation, it would not require any additional effort to inject any medication beyond what is already done in that verification of the appropriateness of the drug administration does not have to be checked with any other system. Furthermore, by using existing syringe pumps, the system and method would not require any special filling caps or system as is done with inhaled drugs when filling vaporizers.

The present invention has been described in terms of specific embodiments incorporating details to facilitate the understanding of the principals of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

What is claimed is:

1. A method of pre-delivery drug identification, the method comprising:
   receiving a drug sample from a drug source into a drug identification unit;
   identifying the drug sample with the drug identification unit;
   collecting a set of patient physiological data with a monitoring device;
   cross-referencing, with a computer, the identified drug sample with the set of patient physiological data such that the set of patient physiological data confirms whether the identified drug sample is safe for the patient;
   cross-referencing, with the computer, the identified drug sample with a set of databases, such that the set of databases confirm whether the identified drug sample is safe for the patient;
   preventing the identified drug sample from being administered to a patient with a delivery prevention unit disposed in fluid connection intermediate the drug identification unit and the patient in response to the set of patient physiological data not confirming that the identified drug sample is safe for the patient; and
   preventing the identified drug sample from being administered to the patient with the delivery prevention unit in response to the set of databases not confirming the identified drug sample.

2. The method according to claim 1, wherein the drug sample corresponds to a prescription for the patient.

3. The method according to claim 1, wherein the identifying step further includes identifying components, a concentration and a dosage of the drug sample.

4. The method according to claim 1, further comprising activating an alarm when the identified drug is prevented from being administered wherein the alarm is any of the following:
   an audible alarm;
   a visual alarm; and
   a remote alarm.

5. The method according to claim 4, further comprising overriding the preventing step when the alarm is activated, thus administering the identified drug to the patient.

6. The method according to claim 1, further comprising confirming the identifying step with an RFID tag and an RFID reader.

7. The method according to claim 1, wherein the drug identification unit is an IR detection system.

8. The method according to claim 1, wherein the monitoring device is any of the following:
   a physiological monitor; and
   a ventilator sensor.

9. A system for pre-delivery drug identification, the system comprising:
   a drug identification unit configured to receive a drug sample from a drug source comprising a supply of a drug, wherein the drug identification unit analyzes the drug sample to produce a drug sample identification;
   a monitoring device collecting a set of patient physiological data from a patient;
   a set of databases comprising drug information indicative of a drug to be delivered to the patient;
   a computer processor coupled to the drug identification unit, the monitoring device, and the set of databases, the computer processor receives the drug sample identification and cross-references the drug sample identification with the set of patient physiological data to determine if administration of the drug is physiologically safe, the computer processor further cross-references the drug sample identification with the drug information of the set of databases to determine if the drug is the drug to be delivered to the patient;
   a delivery prevention unit communicatively coupled to the computer processor and fluidly coupled between the drug identification unit and the patient to receive the drug from the drug identification unit, the computer processor operates the delivery prevention unit to selectively administer the drug to the patient when the computer processor determines the drug is physiologically safe and is the drug to be delivered to the patient.

10. The system according to claim 9, wherein the drug sample corresponds to a prescription for the patient.

11. The system according to claim 9, wherein the drug identification unit is configured to identify components, a concentration and a dosage of the drug sample.

12. The system according to claim 9, further comprising an alarm that is activated when the identified drug is prevented from being administered wherein the alarm is any of the following:
   an audible alarm;
   a visual alarm; and
   a remote alarm.

13. The system according to claim 12, wherein a physician may override the delivery prevention unit when the alarm is activated, thus administering the identified drug to the patient.

14. The system according to claim 9, further comprising an RFID tag and an RFID reader configured to confirm the identification of the drug sample.

15. The system according to claim 9, wherein the drug identification unit is an IR detection system.

16. The system according to claim 9, wherein the monitoring device is any of the following:
   a physiological monitor; and
   a ventilator sensor.

17. A system for pre-delivery drug identification, the system comprising:
   a drug source that provides a drug at a drug dosage;

a drug identification unit, the drug identification unit receives a drug sample from the drug source, and the drug identification unit identifies the drug sample and identifies a dosage of the drug sample;

a monitoring device collecting a set of patient physiological data from a patient;

a set of databases coupled to the drug identification unit, the set of databases comprising at least a prescribed drug identification and a prescribed drug dosage;

a delivery prevention unit fluidly connected between the drug identification unit and a patient;

a storage media for storing a computer application; and a processing unit coupled to the drug identification unit, the monitoring device and the delivery prevention unit, the processing unit receives the drug sample identification and the dosage of the drug sample from the drug identification unit;

wherein when the computer application is executed, the drug sample identification is cross-referenced with the set of patient physiological data, and the delivery prevention unit is instructed to prevent the drug sample from being administered to the patient when the set of patient physiological data does not confirm the drug sample is safe for the patient;

further wherein the processing units cross-references the drug sample identification with the set of databases and operates the delivery prevention unit to prevent the drug sample from being administered to the patient when the drug sample identification does not match the prescribed drug identification; and further wherein the processing unit cross-references the drug dosage identification with the set of databases and operates the delivery prevention unit to prevent the drug sample from being administered to the patient when the dosage of the drug sample does not match the prescribed drug dosage.

\* \* \* \* \*